(12) United States Patent
Medvedev

(10) Patent No.: US 7,160,243 B2
(45) Date of Patent: Jan. 9, 2007

(54) METHOD AND SYSTEM FOR CONTROLLING BLOOD PUMP FLOW

(75) Inventor: Alexander Medvedev, Orange Village, OH (US)

(73) Assignee: Terumo Corporation, Tokyo (JP)

( * ) Notice: Subject to any disclaimer, the term of this patent is extended or adjusted under 35 U.S.C. 154(b) by 154 days.

(21) Appl. No.: 10/808,346

(22) Filed: Mar. 25, 2004

(65) Prior Publication Data

US 2005/0215843 A1  Sep. 29, 2005

(51) Int. Cl.
*A61N 1/362* (2006.01)
(52) U.S. Cl. ....................................................... 600/17
(58) Field of Classification Search .................. 600/16, 600/17, 508; 623/3.1, 3.13
See application file for complete search history.

(56) References Cited

U.S. PATENT DOCUMENTS

| 5,888,242 | A |   | 3/1999 | Antaki et al. |
|---|---|---|---|---|
| 5,947,892 | A | * | 9/1999 | Benkowski et al. ........... 600/16 |
| 7,004,924 | B1 | * | 2/2006 | Brugger et al. ............ 604/6.13 |
| 2004/0152944 | A1 | * | 8/2004 | Medvedev et al. ........... 600/17 |

FOREIGN PATENT DOCUMENTS

WO    WO 01/72352    10/2001

* cited by examiner

*Primary Examiner*—Mark Bockelman

(57) ABSTRACT

A heart assist device, for example a left ventricular assist device (LVAD) including a blood pump, is controlled on the basis of a ratio of the pump's speed and the patient's heart rate. The patient's activity and a required cardiac assist level can be defined via the heart beat rate of the patient and a rotational speed of the LVAD pump. Controlling the pump of the heart assist device based on the pump speed and the patient's heart rate enables the heart assist device to respond to changes in the patient's activity level.

23 Claims, 5 Drawing Sheets

METHOD AND SYSTEM FOR CONTROLLING BLOOD PUMP FLOW

BACKGROUND OF THE INVENTION (1) Field of the Invention

The invention described herein is directed to a method and system for controlling the operation of a blood pump, for example controlling the flow or output of an implantable blood pump that is connected to a patient's circulatory system.

(2) Description of Related Art

U.S. Pat. No. 5,888,242 is directed to an automatic speed control system that continually adjusts the speed of an implanted cardiac assist blood pump to an appropriate level for the varying physiological needs of the patient. It does this by iteratively incrementing the speed setpoint of the pump. When the system detects the imminence of a ventricular collapse at diastole, it decrements the speed setpoint by a predetermined safety margin. An alarm condition is indicated if the setpoint decrease results in an insufficient blood flow rate through the pump. The flow rate and imminence of ventricular collapse are computed in real time as functions of the pump's motor current and speed setpoint.

International Publication No. WO 01/72352 A2 discloses a control system for rotodynamic blood pumps. A left ventricular assist device (LVAD) including a rotodynamic blood pump is powered by a brushless DC motor. Three feedback channels, one for each of voltage, current, and motor speed, provide inputs to a microcontroller or microprocessor. The three feedback waveforms are analyzed, and from these waveforms, motor input power, patient heart rate, current pump flow rate, and systemic pressure are determined. The microprocessor calculates a desired flow rate proportional to the patient heart rate, and communicates a new power output to a commutation circuit, which regulates power to the motor. The pump also includes safety checks that are prioritized over desired pump flow. These include prevention of ventricular suction, low pulsatility, minimum and maximum pump speed, minimum speed-relative pump flow, minimum absolute pump flow, minimum and maximum motor input power.

SUMMARY OF THE INVENTION

Consistent with exemplary embodiments and methods of the present invention, physiologic control of a blood pump, for example a left ventricular assist device (LVAD) including a rotodynamic pump, responds to changing patient activity level while maintaining safe pump operation, to prevent ventricular suction or the like. In a preferred embodiment, the control is based on a ratio of the patient's heart rate to a function of the pump's speed. The patient's activity and a required cardiac assist level can be derived from the heart beat rate of the patient and the rotational speed of the pump, which serves as indirect feedback of systemic afterload.

BRIEF DESCRIPTION OF THE DRAWINGS

The accompanying drawings provide visual representations which are used to more fully describe the representative embodiments disclosed herein, to facilitate a better understanding of the invention and its inherent advantages. In these drawings, like reference numerals identify corresponding elements.

DETAILED DESCRIPTION

To facilitate an understanding of the principles of the present invention, it is described hereinafter with reference to its implementation in an implantable blood pump, such as a Left Ventricular Assist Device (LVAD). While the invention is well suited for a system of this type, it will be appreciated that this is not the only application of the invention. Rather, the principles of the invention can be applied to any type of blood pump in which it is desirable to control the operation of the pump in accordance with the patient's activity level.

Figure 1:
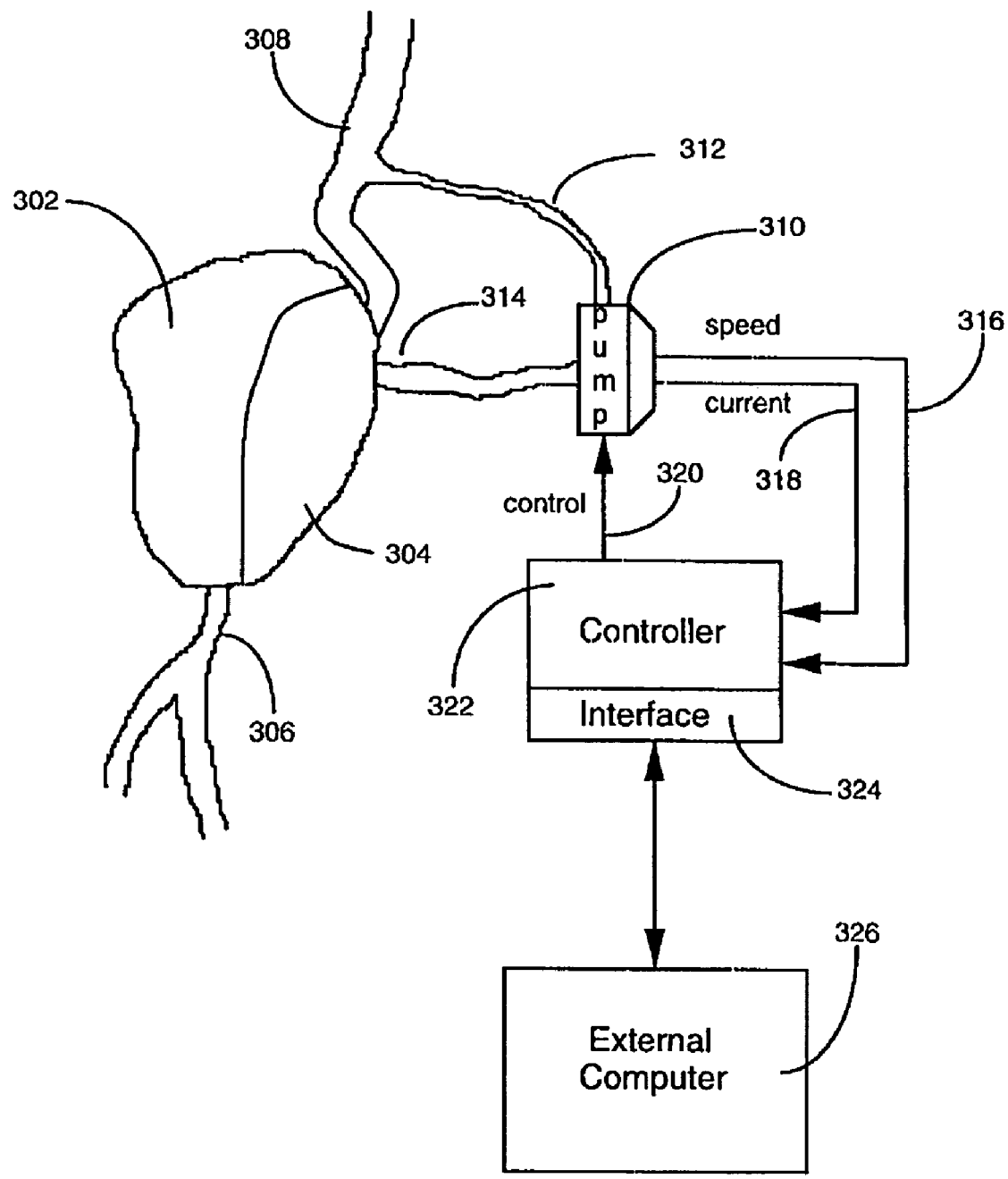
FIG. 1 is a block diagram of an exemplary system in which the present invention can be implemented.

FIG. 1 is a block diagram of an exemplary LVAD system incorporating the principles of the present invention. A patient's heart 302 receives oxygenated blood via the vena cava 306, and the left ventricle 304 pumps the blood into the aorta 308. A pump 310 of the LVAD system removes blood from the left ventricle 304 via an inlet tube 314, and pumps the blood into the aorta 308 via an outlet tube 312. A controller 322 receives a signal 316 indicating the speed of the pump, as well as a signal 318 indicating the amount of electric current being drawn by an electric motor (not shown separately) that is driving the pump. Although the speed and current signals are shown as emanating from the pump itself, the signals can be provided from sensors in any appropriate location and/or configuration. Typically, the current and speed sensors might be located within the controller 322 itself. Consequently, the signal lines 316 and 318 should be viewed as representing information that is obtained from the operation of the pump and/or its driving motor to derive speed and current data.

In response to this input data, the controller 322 produces an output signal 320 that regulates the speed of the pump 310. The control signal 320 can be an analog signal or a digital signal, and can be provided for example to a speed controller located within the pump 310, to a power supply external to the pump 310, or to any mechanism at any location that causes the pump to respond and adjust or maintain its speed in accordance with the control signal 320. The controller 322 can be implemented in various ways, for example as an analog or digital device, as an electronic device including digital logic and/or a microprocessor or microcontroller, or the like. The controller 322 can include any processing or analytical capability necessary to process the feedback information from the pump 310 and perform the control processes described hereinafter.

In one embodiment, such as an LVAD system, the pump 310 and the controller 322 can be a self-contained system that is implanted within the body of the patient. In a variant of this embodiment, the controller 322 can be equipped with an interface 324 for communication with a computer system 326. The computer system 326 can be used to program, monitor or diagnose the controller 322. In the case of an implantable pump system, the interface 324 provides transdermal communication capabilities between the internal pump system and the external computer system 326. In another embodiment, the pump 310 and controller 322 can be located outside the body as well.

Figure 2:
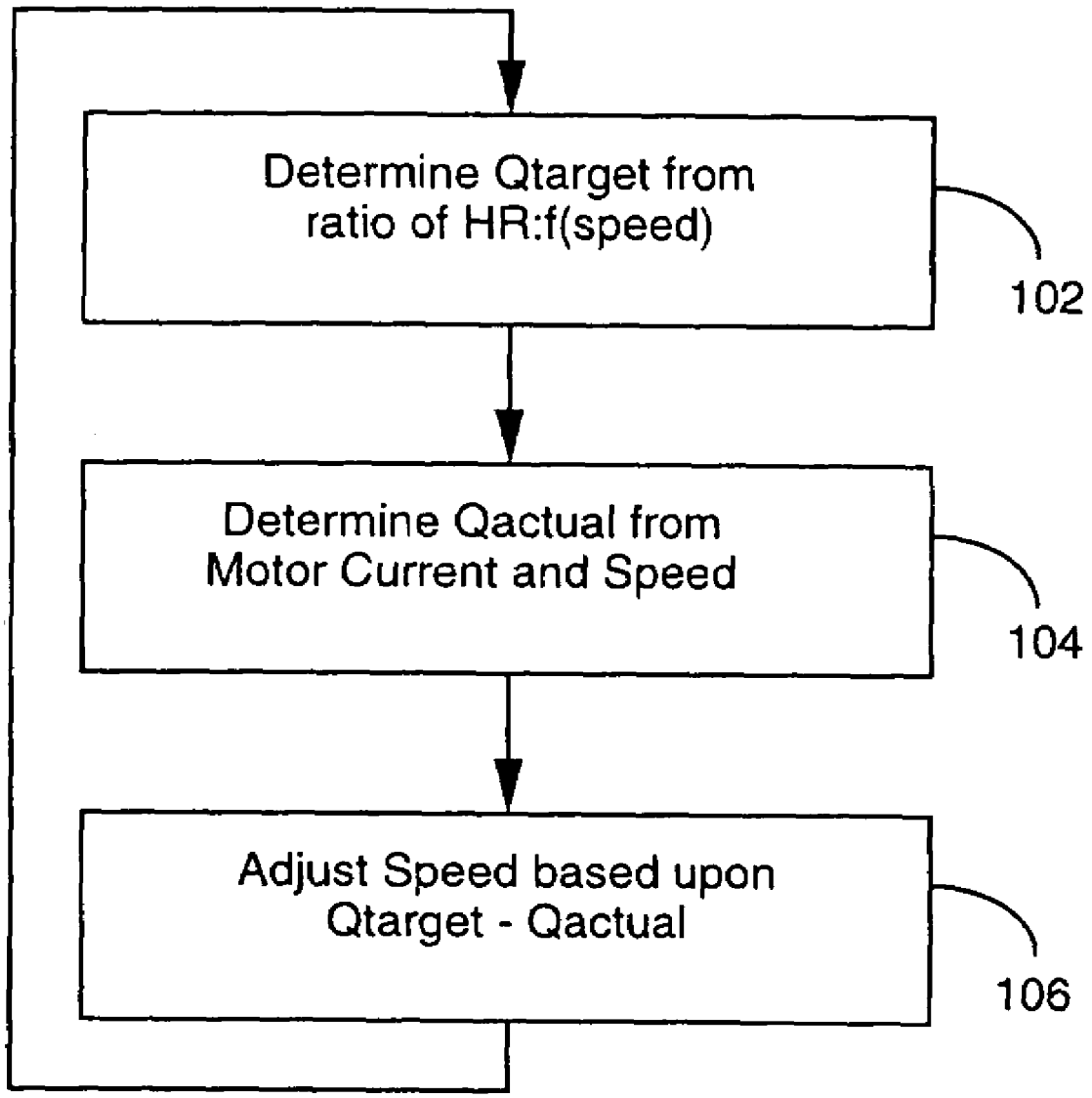
FIG. 2 is a flow chart of an exemplary method for controlling the speed of a blood pump in accordance with the present invention.

The controller 322 includes a read-only memory (ROM) or other suitable program memory storing a control algorithm for generating the control signal 320 that regulates the speed of the pump 310 in accordance with the speed and current input data. FIG. 2 is a flow chart of the general method for controlling the pump 310 in accordance with such an algorithm. Pursuant thereto, at step 102 a target pump flow rate Qtarget is determined on the basis of the ratio of the patient's heart rate and a function of the speed N of the pump. At step 104, the actual flow rate Q is determined from current flow to an electric motor driving the pump, and the speed N of the pump. At step 106, the speed N of the pump is adjusted, based on the difference between the target pump flow rate Qtarget and the actual flow rate Q. Control then returns from step 106 to step 102 to repeat the control cycle. The rate of repetition is programmable, and is based upon the length of a period of time over which the pump speed is expected to remain relatively constant, e.g. 5–20 seconds.

Figure 3A:
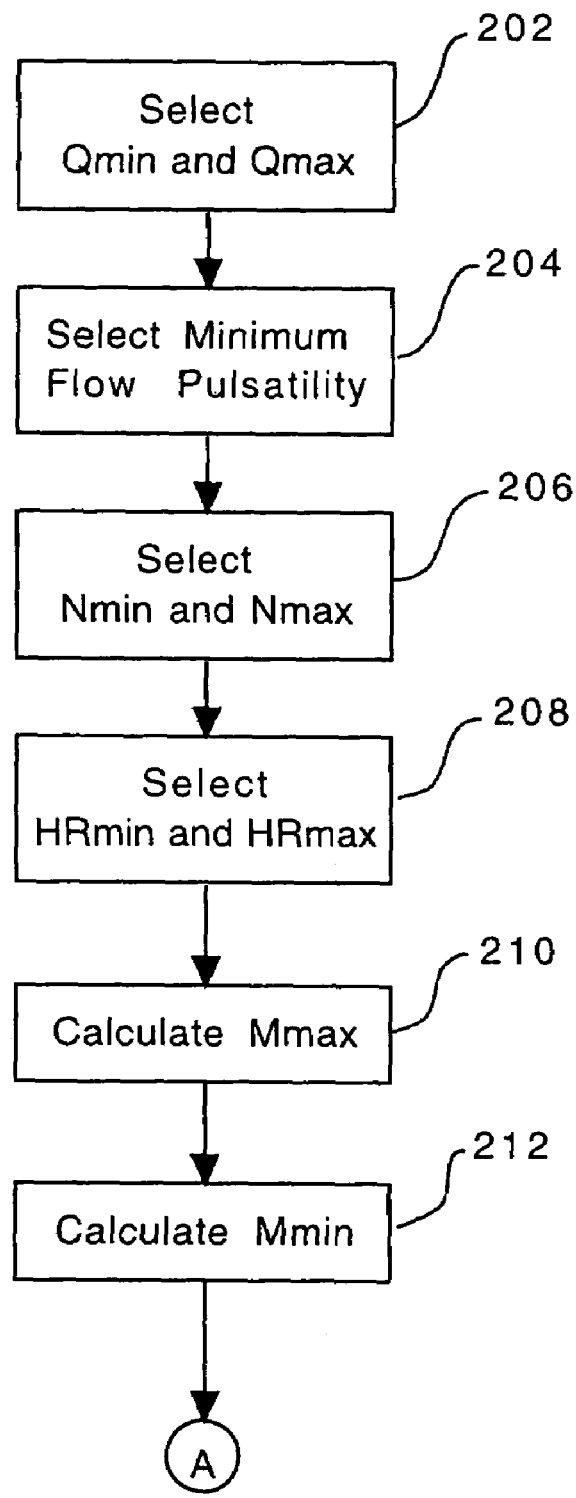
FIGS. 3A–3B illustrate a more detailed example of the method for controlling pump speed.
Figure 3B:
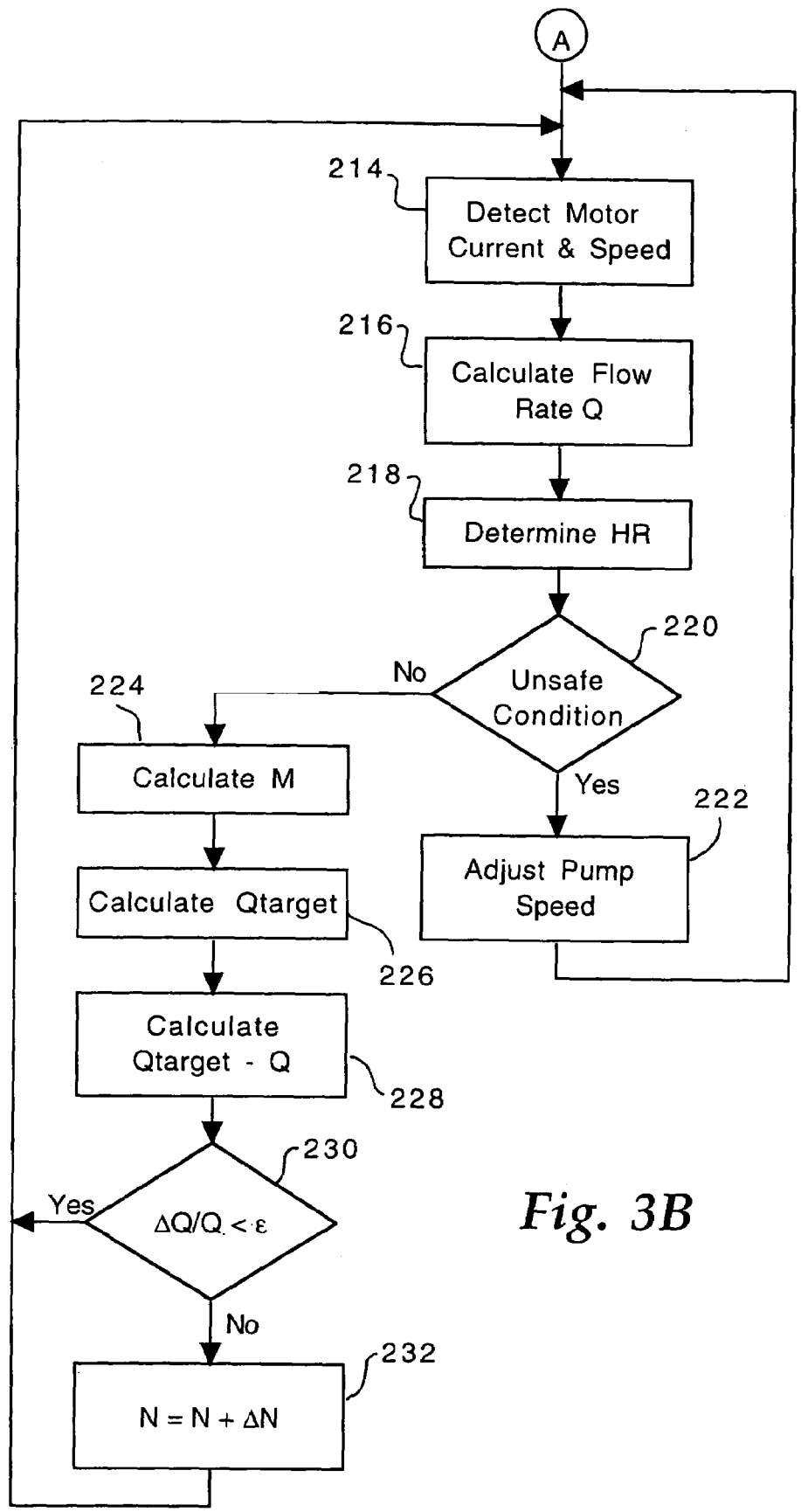

FIGS. 3A–3B illustrate further details of an exemplary implementation of the method shown in FIG. 2. Referring to FIG. 3A, as well as the graph of FIG. 4, in a first step 202, a minimum pump flow rate Qmin and a maximum pump flow rate Qmax are selected by an operator, e.g. the patient's doctor. The pump flow rate can be restricted to stay within these limits at all times. At step 204, a minimum flow pulsatility value is selected. Pulsatility can be defined, for example, as the ratio: (pump flow in systole—mean pump flow rate)/(mean pump flow rate). Pulsatility can also be expressed as a percentage, for example by multiplying this ratio by 100, and can indicate significant unloading of the assisted ventricle that might precede ventricular suction.

At step 206 a minimum pump speed Nmin and a maximum pump speed Nmax are selected. The pump can be controlled to stay within these limits, regardless of physiologic conditions. In step 208, a minimum heart rate HRmin and a maximum heart rate HRmax are selected. In operation, heart rates outside these limits are clamped to the nearest limit by the algorithm. This can be desirable, for example, to mitigate effects of acting on false or incorrect heart rate values.

The values for the minimum and maximum flow rate, pulsatility, pump speed and heart rate can be selected by the doctor on the basis of various physiological factors, such as the patient's size, age and activity level, and programmed into the controller 322. These parameter values are selected so as to prevent complete unloading of the left ventricle, and thereby maintain suitable conditions for aortic valve opening.

In step 210, a maximum ratio Mmax is calculated based on HRmax and f(Nmin). This ratio can, for example, be defined as Mmax=HRmax/(Nmin)$^n$. In a similar manner, at step 212, a minimum ratio Mmin is calculated based on HRmin and f(Nmax). This ratio can, for example, be defined as Mmin=HRmin/(Nmax)$^n$. The power n can be empirically determined on the basis of at least one of the size of the pump and the type of pump. For example, n can be 1 (for a linear function) or 2 (for a quadratic function). Other functions of the speed can also be utilized in determining the ratio M, such as logarithmic, exponential, parabolic, etc., to provide the desired relationship of targeted flow to patient activity level.

Figure 5:
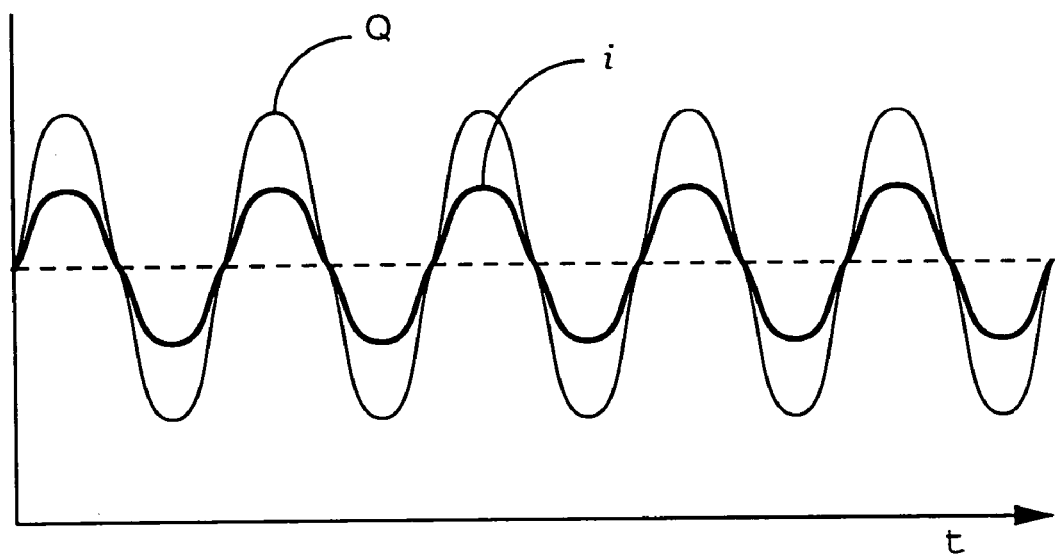
FIG. 5 is a graph of the relationship between motor current and pump flow rate.

At step 214, the electrical current supplied to or consumed by the motor and the speed of the motor are detected. These actions can of course be performed using techniques well known in the electromagnetic art. For example, values can be sampled at selected time intervals to form waveforms depicting the current and the speed over time. The sampling period can, for example, span 5–20 seconds, or any other programmable time interval. The sampling rate can be, for example, 20–30 Hertz, or any other rate. At step 216, a flow rate Q of the pump is calculated on the basis of empirically determined relationships between flow, motor electrical current and motor speed for a given pump. Reference is made to the previously cited U.S. Pat. No. 5,888,242 and WO 01/72352 A2 for examples of this type of calculation. The relationship of motor current i and flow rate Q is depicted in the graph of FIG. 5. As can be seen, the two waveforms have a common frequency, but differ in amplitude. The amount of this difference can be empirically determined for a pump of interest. At step 218, the motor current waveform or the pump flow rate is analyzed to determine the heart rate of the patient. This can be performed, for example, by frequency analysis of the motor current or pump flow waveform to find a fundamental frequency corresponding to the patient's heart rate.

In step 220, a determination is made whether any unsafe conditions are present that could result in ventricular suction. Unsafe conditions can include, for example, the flow pulsatility being less than a programmable threshold value, for example 40%. Another unsafe condition can be a pump flow rate that falls below a programmable minimum value considered to be a minimum safe level for the patient. This minimum safe level can vary from patient to patient. Another unsafe condition can be when the pump flow rate falls below a threshold defined by a predetermined monotonic function that is based on the pump's hydraulic performance. For example, the function can take the form: $F(N)=A+B*N^k$, where N is motor speed. For one exemplary type of pump, A can be 0.8, B can be 0.7, and k can be 2 so that the function will have the following values at various motor speeds: 2.2 LPM (Liters per Minute) @ N=1,400 RPM (Revolutions Per Minute); 2.8 LPM @ N=1,700 RPM; and 3.6 LPM @ N=2,000 RPM.

If the determination in step 220 indicates that unsafe conditions are present, control proceeds to step 222, where the motor speed is changed to remove the unsafe condition. This change can be carried out by adjusting the pump speed by a predetermined percentage, e.g. 4–6%. The adjustment would normally be a decrease of the pump speed, although an increase may be appropriate, in dependence upon the particular unsafe condition that was identified. From step 222, control returns to step 214, to again determine the pump operating parameters at the new pump speed. This process continues in an iterative manner, until the unsafe condition has been removed.

Once a determination is made at step 220 that no unsafe condition is present, the ratio M is calculated at step 224. This ratio is based on the determined heart rate and a function of the mean value of the pump speed N over a time period, for example a control interval defined as a minimum time period over which the pump speed is not changed, e.g. 5–20 seconds. The function of the mean pump speed that is employed at this step is the same as that which was used to calculate Mmax and Mmin in steps 210 and 212. At step 226, a target pump flow rate Qtarget is calculated based on Qmin, Qmax, M, Mmin, and Mmax. As an example, Qtarget can be calculated as:

$$Q\text{target}=Q\text{min}+K*(M-M\text{min}), \text{ where } K=(Q\text{max}-Q\text{min})/(M\text{max}-M\text{min}).$$

Figure 4:
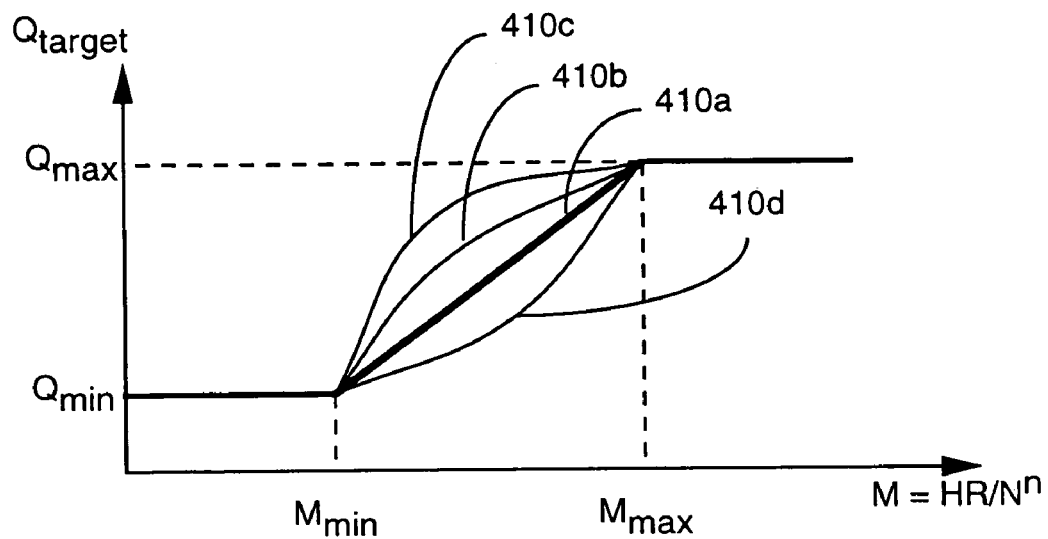
FIG. 4 is a graph illustrating the relationship of the target pump flow rate to the ratio of pump speed and heart rate.

FIG. 4 illustrates the relationship of the target heart rate Q to the ratio M. By virtue of the clamping of heart rates below HRmin and above HRmax to the nearest limit value, the process will always operate within the range of Mmin to Mmax along the horizontal axis. Consequently, the target flow rate Q will be determined by any one of functions 410a, 410b, 410c, or 410d whose values lie within the range between Qmin and Qmax. Any monotonic function can be employed to define the relationship between the target flow rate and the ratio M. As a default, a linear function might be employed, as depicted by the solid line 410a. However, if the doctor determines that a flow rate is preferred, a non-linear function such as those depicted by the lines 410b or 410c might be selected. Conversely, if a relatively low flow rate is more desirable, e.g. the patent only requires assistance at high activity levels, a function such as that represented by line 410d can be selected.

At step 228, a difference between Qtarget and Q is calculated. A determination is made at step 230 whether the actual pump flow rate Q is within a predetermined accuracy level of Qtarget. The accuracy interval can be defined as: $(|Q-Qtarget|)/Q \leq \epsilon$, where $\epsilon$ is the selected accuracy. The value for $\epsilon$ can be selected on the basis of the type of pump and its application. For instance, it might be a value of 5% for an LVAD application, but a smaller value for an RVAD pump, which operates at lower pressures. If the determination at step 230 is yes, control returns to step 214, where the control process starts anew.

If the difference between Q and Qtarget is outside the predetermined accuracy level, the pump speed N is changed at step 232, based on the calculated difference between Qtarget and Q. The pump speed adjustment performed in step 232 can be performed as follows:

$$N\text{new} = N + \Delta N$$

where $$\Delta N = \lambda * \Delta Q/Q$$

and where $\lambda$ is a predetermined function of $\Delta Q$: e. g. $\lambda = 0.1 + (\Delta Q/Q)^2$.

The maximum pump speed step change can be limited, for example to 5% of the pump's actual speed value N, e.g., $\Delta N \leq 0.05*N$.

Control then returns to step 214, where the process is then repeated for the next control cycle after a suitable delay, e.g. 5–20 seconds.

It will be appreciated by those skilled in the art that the present invention can be embodied in other specific forms without departing from the spirit or essential characteristics thereof, and that the invention is not limited to the specific embodiments described herein. The presently disclosed embodiments are therefore considered in all respects to be illustrative and not restrictive. The scope of the invention is indicated by the appended claims rather than the foregoing description, and all changes that come within the meaning and range and equivalents thereof are intended to be embraced therein.

The invention claimed is:

1. A method for controlling a blood pump connected to a patient, comprising the following steps:
    determining a value for the heart rate of the patient;
    determining a value for the speed of the pump;
    calculating the ratio of said heart rate value and said speed value; and
    regulating the speed of the pump in accordance with said ratio.

2. The method of claim 1, wherein the speed of the pump is regulated to achieve a target flow rate that is a monotonic function of said ratio within a defined range of flow rates.

3. The method of claim 2, wherein said monotonic function is linear, and
    said target flow rate Qtarget=$K_1$*M+$K_2$
    where M=HR/f(N), HR is the patient's heart rate, N is the speed of the pump, and $K_1$, $K_2$ are constants.

4. The method of claim 3 wherein f(N)=$N^n$, where n is related to at least one of a type and size of the pump.

5. The method of claim 3, wherein:
    $K_1$=(Qmax−Qmin)/(Mmax−Mmin); and
    $K_2$=Qmin−(Qmax−Qmin)*Mmin/(Mmax−Mmin);
    where Qmax is a maximum allowable flow rate of the pump, Qmin is a minimum allowable flow rate of the pump, Mmax is a maximum threshold value of the ratio M, and Mmin is a minimum threshold value of the ratio M.

6. The method of claim 5, wherein:
    Mmax=HRmax/(Nmin)$^n$; and
    Mmin=HRmin/(Nmax)$^n$.

7. The method of claim 1, further comprising the step of:
    changing the pump speed when flow pulsatility falls below a defined threshold.

8. The method of claim 7, wherein said threshold is a predefined monotonic function based on hydraulic performance of the pump.

9. The method of claim 7, wherein the step of changing the pump speed is carried out prior to the step of regulating the speed of the pump in accordance with said ratio.

10. A blood pump system for assisting a patient's heart, the system comprising:
    a blood pump adapted to be connected to the patient; and
    a controller that receives input signals, determines a pump speed value and a patient heart rate value from said input signals, determines a ratio of the patient's heart rate value and the pump speed value, and regulates the pump speed based upon said determined ratio.

11. The system of claim 10, wherein the controller regulates the speed of the pump to achieve a target flow rate that is a monotonic function of said ratio within a defined range of flow rates.

12. The system of claim 11, wherein said monotonic function is linear, and
    said target flow rate Qtarget=$K_1$*M+$K_2$
    where M=HR/f(N), HR is the patient's heart rate, N is the speed of the pump, and $K_1$, $K_2$ are constants.

13. The system of claim 12, wherein f(N)=$N^n$, where n is related to at least one of a type and size of the pump.

14. The system of claim 12, wherein:
    $K_1$=(Qmax−Qmin)/(Mmax−Mmin); and
    $K_2$=Qmin−(Qmax−Qmin)*Mmin/(Mmax−Mmin);
    where Qmax is a maximum allowable flow rate of the pump, Qmin is a minimum allowable flow rate of the pump, Mmax is a maximum threshold value of the ratio M, and Mmin is a minimum threshold value of the ratio M.

15. The system of claim 14, wherein:
    Mmax=HRmax/(Nmin)$^n$; and
    Mmin=HRmin/(Nmax)$^n$.

16. The system of claim 10, wherein the controller changes the pump speed when flow pulsatility falls below a first threshold.

17. The system of claim 16, wherein said threshold is a predefined monotonic function based on hydraulic performance of the pump.

18. The system of claim 16, wherein the controller performs said changing of pump speed prior to regulating the speed of the pump based on said ratio.

19. A machine readable medium comprising a computer program that receives input signals, determines a value of the speed of a blood pump connected to a patient and a value of the patient's heart rate from said input signals, determines a ratio of the patient's heart rate to the speed of the pump, and regulates the pump speed based upon said ratio.

20. The machine-readable medium of claim 19, wherein the speed of the pump is regulated to achieve a target flow rate that is a monotonic function of said ratio within a defined range of flow rates.

21. The medium of claim 19, wherein:
said target flow rate $Qtarget = K_1 * M + K_2$,
where $M = HR/N^n$, HR is the patient's heart rate, N is the speed of the pump, n is related to at least one of a type and size of the pump, and $K_1$, $K_2$ are constants.

22. The medium of claim 21, wherein:
$K_1 = (Qmax - Qmin)/(Mmax - Mmin)$; and
$K_2 = Qmin - (Qmax - Qmin) * Mmin/(Mmax - Mmin)$;
where Qmax is a maximum allowable flow rate of the pump, Qmin is a minimum allowable flow rate of the pump, Mmax is a maximum threshold value of the ratio M, and Mmin is a minimum threshold value of the ratio M.

23. The medium of claim 22, wherein:
$Mmax = HRmax/(Nmin)^n$; and
$Mmin = HRmin/(Nmax)$.

\* \* \* \* \*